United States Patent
Shiiba et al.

(10) Patent No.: US 6,743,459 B2
(45) Date of Patent: Jun. 1, 2004

(54) ACIDIC OIL-IN-WATER TYPE EMULSION COMPOSITION

(75) Inventors: Daisuke Shiiba, Tokyo (JP); Yoshihide Asabu, Tokyo (JP); Shigeru Kawai, Tokyo (JP); Yoshinobu Nakajima, Tokyo (JP)

(73) Assignee: Kao Corporation, Tokyo (JP)

(*) Notice: Subject to any disclaimer, the term of this patent is extended or adjusted under 35 U.S.C. 154(b) by 257 days.

(21) Appl. No.: 10/014,356

(22) Filed: Dec. 14, 2001

(65) Prior Publication Data

US 2002/0119239 A1 Aug. 29, 2002

(30) Foreign Application Priority Data

Dec. 15, 2000 (JP) ......................................... 2000-381596

(51) Int. Cl.$^7$ ................................................. A23D 7/00
(52) U.S. Cl. ..................... 426/602; 426/611; 426/604
(58) Field of Search ............................... 426/602, 604, 426/605, 611–613

(56) References Cited

U.S. PATENT DOCUMENTS

| | | | |
|---|---|---|---|
| 4,976,984 A | * 12/1990 | Yasukawa et al. | 426/602 |
| 5,160,759 A | * 11/1992 | Nomura et al. | 426/602 |
| 5,340,600 A | 8/1994 | Reckweg et al. | |
| 5,660,865 A | 8/1997 | Pedersen et al. | |
| 6,004,611 A | 12/1999 | Gotoh et al. | |
| 6,337,414 B1 | 1/2002 | Sugiura et al. | |
| 6,399,137 B1 | * 6/2002 | Dartey et al. | 426/602 |
| 6,630,189 B2 | * 10/2003 | Sugiura et al. | 426/330.6 |
| 6,635,777 B1 | * 10/2003 | Kawai et al. | 554/227 |
| 2002/0025370 A1 | * 2/2002 | Sugiura et al. | 426/602 |

FOREIGN PATENT DOCUMENTS

| | | |
|---|---|---|
| EP | 0 378 893 | 7/1990 |
| EP | 0 402 090 | 12/1990 |
| EP | 0 750 848 | 1/1997 |
| EP | 0 836 805 | 4/1998 |
| EP | 0 990 391 | 4/2000 |
| EP | 1 135 991 | 9/2001 |
| JP | 3-8431 | 1/1991 |
| JP | 3-91451 | 4/1991 |
| JP | 4-79858 | 3/1992 |
| JP | 4-300828 | 10/1992 |
| JP | 10-176181 | 6/1998 |
| WO | WO 00/78162 | 12/2000 |
| WO | WO 01/01787 | 1/2001 |
| WO | WO 01/15542 | 3/2001 |

OTHER PUBLICATIONS

Derwent Abstracts of Japan, AN1987–294789, XP–00219090, JP 62–205738, Sep. 10, 1987.

Derwent Abstracts of Japan, AN 1998–072028, XP–002196091, JP 09–310088, Dec. 2, 1997.

Derwent Abstracts of Japan, AN–1992–142505, XP–002196208, JP 04–264033, Sep. 18, 1992.

* cited by examiner

Primary Examiner—Carolyn Paden
(74) Attorney, Agent, or Firm—Oblon, Spivak, McClelland, Maier & Neustadt, P.C.

(57) ABSTRACT

The invention provides an acidic oil-in-water type emulsion composition which has an oil phase containing at least 20 % by weight of diacylglycerol and 0.5 to 5.0 % by weight of a crystallization inhibitor, and has excellent shelf stability at low temperatures though it contains diacylglycerol at a high concentration, also good in appearance and flavor and useful as a diet or food for improving lipid metabolism.

6 Claims, No Drawings

ACIDIC OIL-IN-WATER TYPE EMULSION COMPOSITION

BACKGROUND OF THE INVENTION

1. Field of the Invention

The present invention relates to an acidic oil-in-water type emulsion composition such as mayonnaise or dressing, which is excellent in emulsion stability even under low-temperature conditions such as in side refrigerators, good in appearance and flavor and useful as diet or food for improving lipid matabolism.

2. Description of the Background Art

In recent years, it has been clarified that diacylglycerol (hereafter referred to as "DAG") has an obesity-preventing effect, an effect to prevent increase in weight, etc. (Japanese Patent Application Laid-Open No. 300828/1992, etc.), and it is attempted to incorporate this into various kinds of foods (Japanese Patent Application Laid-Open Nos. 8431/1991, 79858/1992 and 176181/1998, etc.). Furthermore, oil-in water type emulsions containing DAG and lecithin in an oil phase and protein in a water phase have been proposed (Japanese Patent Application Laid-Open No. 91451/1991).

In the case of, particularly, an acidic oil-in-water type emulsion composition such as mayonnaise or dressing, however, the low-temperature resistance has been insufficient in that a part of DAG in raw oil crystallizes under in-refrigerator conditions (−5 to 5° C.) that cause demulsification (oil-off), and for mayonnaise, cracks were observed.

SUMMARY OF THE INVENTION

It is therefore an object of the present invention to provide an acidic oil-in-water type emulsion composition which has excellent shelf stability at low temperatures though containing DAG at a high concentration, also good in appearance and flavor and useful as a diet or food for improving lipid metabolism.

The present inventors have found that an acidic oil-in-water type emulsion composition satisfying the above requirements can be provided by containing a specified amount of crystallization inhibitors in an oil phase containing DAG.

Thus, according to the present invention, we inventors have provided an acidic oil-in-water type emulsion composition comprising an oil phase containing at least 20% by weight of diacylglycerol and 0.5 to 5.0% by weight of a crystallization inhibitor.

DETAILED DESCRIPTION OF THE PREFERRED EMBODIMENTS

DAG used in the present invention is obtained by esterifying hydroxyl groups at 1- and 2-positions or 1- and 3-positions of glycerol with fatty acids. The number of carbon atoms in fatty acid residues are preferably (but not limited to) 8 to 24, particularly 16 to 22. The amount of unsaturated fatty acid residues is preferably at least 55%, more preferably at least 70%, most preferably at least 90% based on all the fatty acid residue. DAG is obtained by any known process such as ester exchange reaction of vegetable oil and/or animal oil with glycerol or esterification reaction of fatty acids derived from the above oil with glycerol. The reaction method thereof may be either a chemical reaction by the aid of alkali catalysts, for example, or a biochemical reaction method using oil and/or fat hydrolase such as lipase. One or blends of such DAGs may be used. The content of DAG in the oil phase must be at least 20% by weight, preferably at least 35% by weight from the viewpoints of effectiveness as a diet and profitability. The oil phase may contain triacylglycerol, monoacylglycerol, fatty acids and the like in addition to DAG. These may be derived from any of vegetable oils and/or animal oils.

Examples of raw oil include vegetable oils such as soybean oil, rapeseed oil, sunflower oil, cotton-seed oil, corn oil, safflower oil, linseed oil, olive oil, rice oil and palm oil; animal oils such as beef tallow, lard and fish oil; which may be further fractionated or transesterified.

The oil phase content in the acidic oil-in-water type emulsion composition is preferably 5 to 85% by weight, more preferably 10 to 80% by weight, particularly preferably 20 to 80% by weight. In particular, the oil phase in the mayonnaise-type composition is preferably 20 to 85% by weight, more preferably 25 to 80% by weight, particularly preferably 30 to 80% by weight. The oil phase content in the dressing-type composition is preferably 5 to 60% by weight, more preferably 10 to 55% by weight, most preferably 20 to 50% by weight.

The crystallization-inhibitor used in the present invention is preferably selected from polyglycerol fatty acid esters, sucrose fatty acid esters and sorbitan fatty acid esters. The polyglycerol fatty acid esters are preferably those in which the average polymerization degree of glycerol is 2 to 12, the number of carbon atoms in the fatty acid moiety is 12 to 22, and the degree of esterification is at least 70%. Furthermore, the HLB of polyglycerol fatty acid esters is preferably lower than 4.5, most preferably lower than 3.5. In the present invention, the average polymerization degree (Mw) is determined by the following equation from the relationship between the polymerization degree (n) and hydroxyl value (OHV) of polyglycerol and the theoretical value.

$$OHV = 56110(n+2)/Mw$$

$$Mw = 74n + 18$$

The sucrose fatty acid esters are preferably those in which the degree of esterification with fatty acids having 12 to 22 carbon atoms is at least 50%, and the remaining hydroxyl groups (not esterified with above-mentioned fatty acids) are acetylated. Furthermore, the sucrose fatty acid esters preferably have an HLB lower than 3, more preferably lower than 2. The sorbitan fatty acid esters are preferably those in which the number of carbon atoms in the fatty acid moiety is 12 to 22, and the HLB is lower than 3, more preferably lower than 2.5. One or more of these crystallization inhibitors may be used, and the content thereof must be 0.5 to 5.0% by weight, preferably 0.6 to 3.0% by weight from the viewpoints of sufficient crystallization-inhibiting effect at low temperatures and flavor as food. The polyglycerol fatty acid esters are particularly preferred from the viewpoint of crystallization-inhibiting effect at varied temperatures.

The water phase in the acidic oil-in-water type emulsion composition according to the present invention may contain water; vinegar; common salt; condiments such as sodium glutamate; saccharides such as sugar and starch syrup; seasonings such as sake and sweet sake; various kinds of vitamins; organic acids; spices; various kinds of vegetables or fruits; thickeners such as xanthan gum; dairy products such as milk; various kinds of fruit juices; proteins such as soybean protein; various kinds of phosphates; etc.

Yolk may be used in the acidic oil-in-water type emulsion composition according to the present invention for the purpose of emulsifying and improving flavor. Yolk may be used in any form such as raw, frozen, powdery, salted or sugared. Furthermore, it may also be used in the form of the whole egg containing egg white. The content of the yolk in the acidic oil-in-water type emulsion composition according to the present invention is preferably 5 to 20%, more preferably 7 to 17%, most preferably 8 to 15% based on weight of raw yolk, from the viewpoint of improvement in flavor.

In the acidic oil-in-water type emulsion composition according to the present invention, a proportion (hereafter referred to as "lyso proportion") of lysophospholipid to total phospholipids contained is preferably at least 15%, more preferably at least 25%, most preferably 29 to 60% from the viewpoints of shelf stability, appearance and flavor. A part or the whole of the lysophospholipid is preferably derived from yolk and/or soybean, most preferably from yolk. Furthermore, a part or the whole of the lysophospholipid is preferably enzyme-treated yolk. The enzyme used in the enzyme treatment of yolk is preferably esterase, lipase or phospholipase, more preferably lipase or phospholipase, most preferably phospholipase. Among various kinds of phospholipases, phospholipase A, i.e., phospholipase A1 or A2 is most preferred.

The acidic oil-in-water type emulsion composition according to the present invention preferably has a pH of 2.5 to 5.0, more preferably 3.0 to 4.5, most preferably 3.4 to 4.2.

The acidic oil-in-water type emulsion composition according to the present invention can be produced in accordance with, for example, the following process. Oil components such as DAG and the crystallization inhibitors are first mixed to prepare an oil phase. Yolk and other water-soluble raw materials are then mixed to prepare a water phase. The oil phase is added to the water phase, and the mixture is homogenized following preliminary emulsification if needed, whereby an acidic oil-in-water type emulsion composition can be obtained. Examples of homogenizers include high-pressure homogenizers such as Mountaingorin and Microfluidizer, ultrasonic emulsifiers, colloid mills, agitating homomixers, and Milder.

The average droplet diameter of oil droplets in the acidic oil-in-water type emulsion composition produced in such a manner is preferably 0.5 to 40.0 μm, more preferably 1.0 to 15.0 μm, most preferably 1.5 to 12.0 μm when measured by a laser diffraction method (using a laser diffraction particle size analyzer).

When the acidic oil-in-water type emulsion composition according to the present invention is mayonnaise or dressing, it is more preferable to have the following average droplet diameter. In the case of mayonnaise, the average droplet diameter is preferably 0.5 to 20.0 μm, more preferably 1.0 to 15.0 μm, most preferably 1.5 to 10.0 μm. In the case of dressing, the average droplet diameter is preferably 0.5 to 40.0 μm, more preferably 1.0 to 40.0 μm, most preferably 5.0 to 40.0 μm.

Examples of product form of the acidic oil-in-water type emulsion composition according to the present invention include those defined by JAS as dressing, semi-solid dressing, emulsified liquid dressing, mayonnaise, salad dressing and French dressing, but not limited to. All kinds of products, widely accepted as mayonnaise and dressing, correspond thereto.

In the following examples, the HLB of the crystallization inhibitors was calculated out in accordance with the Griffin's empirical equation for polyglycerol fatty acid esters, and sorbitan fatty acid esters. For sucrose fatty acid esters, emulsification method was used to determine HLB.

REFERENTIAL EXAMPLE 1
Preparation of Oil Composition 1

Lipozyme IM (product of Novo Nordisk Industry Co.) was added to a mixture of rapeseed oil fatty acid (650 parts by weight) and glycerol (107 parts by weight) and subjected to esterification reaction at 40° C. for 5 hours under 7 hPa. The resultant reaction mixture was then subjected to molecular distillation (235° C., 0.07 hPa) The distillate thus obtained was then bleached, washed with water and deodorized at 235° C. for 2 hours to obtain Oil Composition 1 having a composition shown in Table 1.

REFERENTIAL EXAMPLE 2
Preparation of Oil Composition 2

A mixture of soybean oil fatty acid (650 parts by weight), after the content of saturated fatty acids had been reduced by winterization, glycerol (107 parts by weight) and calcium hydroxide (2 parts by weight) was reacted at 230° C. for 0.5 hours under nitrogen gas atmosphere, the reaction mixture was allowed to stand for 12 hours to separate the glycerol phase, and then the resultant oil phase (oil composition) was washed with a 50% (by weight) aqueous solution of citric acid whose proportion was 2 parts by weight to 100 parts by weight of the oil phase followed by centrifugation to afford oil composition. The resultant oil composition was then subjected to molecular distillation (235° C., 0.07 hPa), and the distillate thus obtained was then bleached, washed with water and deodorized at 235° C. for 2 hours to obtain Oil Composition 2 having a composition shown in Table 1.

TABLE 1

|  |  | Oil composition | |
|---|---|---|---|
|  |  | 1 | 2 |
| Composition of *1 oil | Triacylglycerol | 13.8 | 13.5 |
|  | Diacylglycerol | 84.7 | 85.2 |
|  | Monoacylglycerol | 1.2 | 1.0 |
|  | Free fatty acid | 0.3 | 0.3 |
| Fatty acid *2 composition | C16: 0 | 4.2 | 2.6 |
|  | C18: 0 | 1.9 | 0.7 |
|  | C18: 1 | 58.3 | 30.0 |
|  | C18: 2 | 21.3 | 57.5 |
|  | C18: 3 | 10.7 | 6.8 |
|  | C20: 0 | 0.7 | 1.5 |
|  | C20: 1 | 1.8 | 0.4 |
|  | C22: 0 | 0.2 | 0.1 |
|  | C22: 1 | 0.8 | 0.1 |

*1 Analyzed by gas chromatography after silylation.
*2 Analyzed by gas chromatography after methylation (Number of carbon atoms in fatty acid: number of carbon—carbon double bonds).

REFERENTIAL EXAMPLE 3
Preparation 1 of Enzyme-Treated Yolk

A yolk solution (750 g) containing common salt (10% by weight) was mixed with water (250 g). After the resultant mixture was preheated at 50° C. for 10 minutes, Phospholipase A2 (enzymatic activity: 10,000 IU/mL) was added to the mixture. The proportion of phospholipase to yolk solution was 100 ppm. Reaction was carried out for 3 to 5 hours, thereby obtaining Enzyme-treated Yolk Solution 1.

After a yolk solution (850 g) containing common salt (10% by weight) was mixed with water (150 g), and the resultant mixture was heated to 50° C., the above-described Phospholipase A2 was added to the mixture. The proportion of phospholipase to the yolk solution was 40 ppm. Reaction was carried out for 20 hours, thereby obtaining Enzyme-treated Yolk Solution 2.

After a yolk solution (850 g) containing common salt at a concentration of 10% by weight was mixed with water (150 g), and the resultant mixture was preheated to 50° C., Phospholipase A1 (enzymatic activity: 4,000 IU/mL) was added to the mixture. The proportion of phospholipase to the yok solution was 200 ppm. Reaction was carried out for 5 hours, thereby obtaining Enzyme-treated Yolk Solution 3.

The lyso proportion was calculated out in accordance with the following method.

The reaction product was extracted repeatedly with a mixed solvent (3:1) of chloroform:methanol to obtain a lipid mixture. The resultant lipid mixture was subjected to thin layer chromatography to separate various kinds of phospholipids by two-dimensional thin layer chromatography of the first dimension: chloroform-methanol-water (65:25:49) and the second dimension: butanol-acetic acid-water (60:20:20). The amounts of the separated phospholipids were measured by means of a commercially available measuring kit (permanganate ashing method, Phospholipid Test Wako, trade name; product of Wako Pure Chemical Industries, Ltd.) to calculate out contents of lysophospholipids and total phospholipids. The lyso proportion (%) was defined as "(total amount of phosphorus in lysophospholipid fraction/total amount of phosphorus in all phospholipid fractions)×100".

REFERENTIAL EXAMPLE 4

Preparation 2 of Enzyme-Treated Yolk

Twice amount of water by volume was added to Enzyme-treated Yolk Solution 1 obtained in Referential Example 3 and stirred. The mixture was then spray-dried under air (inlet air temperature=170° C., outlet air temperature=70° C.) to obtain enzyme-treated yolk powder. Examples 1 to 13 and Comparative Examples 1 to 6

Oil phases and water phases of their corresponding compositions shown in Tables 2 and 3 were prepared in a conventional manner. After each of the oil phases was added to its corresponding water phase while stirring the water phase to preliminarily emulsify the oil phase, the emulsion was homogenized by a colloid mill (5,000 rpm, clearance: 0.35 mm) to prepare mayonnaise having an average emulsified droplet diameter of 2.5 to 3.5 μm. The mayonnaise was charged into a mayonnaise tube (100 g). In respect to Example 11 and Comparative Example 4, each mayonnaise was prepared having the average droplet diameter of 8.1 to 9.5 and then charged into a mayonnaise tube (100 g) Mayonnaise samples thus obtained were stored for 1 month to test under low temperature (−5, 0 and 5° C.) and programmed temperature (max 25° C., min 0° C.) and then left to stand at room temperature for 3 hours. Thereafter, the appearances and physical properties thereof were evaluated by 6 panels in accordance with the following evaluation standards. The average values of these evaluations are shown in Table 2.

Evaluation Standards (1) Appearance

The appearance of each mayonnaise sample charged into a tube was visually evaluated.

3: Good;

2: Signs of separation was observed;

1: Obvious separation has taken place.

(2) Physical Property

The mayonnaise sample squeezed out of the tube was visually evaluated

3: Good;

2: Signs of roughening on the surface and/or water separation was observed;

1: Obvious roughening on surface and/or water separation has taken place.

TABLE 2

| | | (% by weight) Example | | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 | 13 |
| Water phase | Common salt | 0.3 | 0.3 | 0.3 | 0.3 | 0.3 | 0.3 | 0.3 | 0.3 | 0.3 | 0.3 | 3.0 | 1.2 | 1.8 |
| | Sucrose | 1.0 | 1.0 | 1.0 | 1.0 | 1.0 | 1.0 | 1.0 | 1.0 | 1.0 | 1.0 | 1.0 | 6.0 | 1.5 |
| | Condiment | 0.4 | 0.4 | 0.4 | 0.4 | 0.4 | 0.4 | 0.4 | 0.4 | 0.4 | 0.4 | 0.5 | — | 0.5 |
| | Mustard powder | 0.2 | 0.2 | 0.2 | 0.2 | 0.2 | 0.2 | 0.2 | 0.2 | 0.2 | 0.2 | 0.3 | 0.2 | 0.3 |
| | Thickener *1 | 0.2 | 0.2 | 0.2 | 0.2 | 0.2 | 0.2 | 0.2 | 0.2 | — | 0.2 | 0.6 | — | 0.6 |
| | Thickener *2 | — | — | — | — | — | — | — | — | 0.2 | — | — | — | — |
| | Thickener *3 | — | — | — | — | — | — | — | — | — | — | — | 1.5 | 2.0 |
| | Soybean protein | — | — | — | — | — | — | — | — | — | — | 1.5 | — | — |
| | Enzyme-treated yolk 1 | 20.0 | 20.0 | 20.0 | 20.0 | 20.0 | 20.0 | — | — | 20.0 | — | — | — | — |
| | Enzyme-treated yolk 2 | — | — | — | — | — | — | — | — | — | — | — | 7.0 | — |
| | Enzyme-treated yolk 3 | — | — | — | — | — | — | — | — | — | — | — | — | 20.0 |
| | Enzyme-treated yolk powder | — | — | — | — | — | — | 7.4 | 3.7 | — | — | — | — | — |
| | Yolk | — | — | — | — | — | — | — | 7.5 | — | 15.0 | — | — | — |
| | 10% Brewed vinegar | 6.0 | 6.0 | 6.0 | 6.0 | 6.0 | 6.0 | 6.0 | 6.0 | 6.0 | 6.0 | 9.0 | 9.5 | 9.0 |
| | Water | 1.9 | 1.9 | 1.9 | 1.9 | 1.9 | 1.9 | 14.5 | 10.7 | 1.9 | 6.9 | 28.1 | 29.6 | 33.3 |
| Oil phase | Oil Composition 1 | 20.7 | 20.5 | 19.5 | 20.5 | 20.5 | 34.5 | 20.5 | 20.5 | 20.5 | 20.5 | 16.5 | 13.2 | 9.0 |
| | Oil Composition 2 | 48.7 | 48.5 | 47.5 | 48.5 | 48.5 | 34.5 | 48.5 | 48.5 | 48.5 | 48.5 | 38.5 | 30.8 | 21.0 |
| | Polyglycerol fatty acid ester *4 | 0.6 | 1.0 | 3.0 | — | — | 1.0 | 1.0 | 1.0 | 1.0 | 1.0 | 1.0 | 1.0 | 1.0 |
| | Sorbitan fatty acid ester *5 | — | — | — | 1.0 | — | — | — | — | — | — | — | — | — |
| | Sucrose fatty acid ester *6 | — | — | — | — | 1.0 | — | — | — | — | — | — | — | — |
| Lyso proportion (%) | | 45 | 45 | 45 | 45 | 45 | 50 | 55 | 55 | 50 | — | — | 55 | 50 |
| Evaluation 5° C. | Appearance | 3.0 | 3.0 | 3.0 | 3.0 | 3.0 | 3.0 | 3.0 | 3.0 | 3.0 | 3.0 | 3.0 | 3.0 | 3.0 |
| | Physical property | 3.0 | 3.0 | 3.0 | 3.0 | 3.0 | 3.0 | 3.0 | 3.0 | 3.0 | 3.0 | 3.0 | 3.0 | 3.0 |
| 0° C. | Appearance | 3.0 | 3.0 | 3.0 | 3.0 | 3.0 | 3.0 | 3.0 | 3.0 | 3.0 | 3.0 | 3.0 | 3.0 | 3.0 |
| | Physical property | 3.0 | 3.0 | 3.0 | 3.0 | 3.0 | 3.0 | 3.0 | 3.0 | 3.0 | 3.0 | 3.0 | 3.0 | 3.0 |
| −5° C. | Appearance | 3.0 | 3.0 | 3.0 | 3.0 | 3.0 | 3.0 | 3.0 | 3.0 | 3.0 | 3.0 | 3.0 | 3.0 | 3.0 |
| | Physical property | 3.0 | 3.0 | 3.0 | 3.0 | 3.0 | 3.0 | 3.0 | 3.0 | 3.0 | 3.0 | 3.0 | 3.0 | 3.0 |
| Cycle test | Appearance | 3.0 | 3.0 | 3.0 | 2.5 | 2.5 | 3.0 | 3.0 | 3.0 | 3.0 | 3.0 | 3.0 | 3.0 | 3.0 |
| | Physical property | 3.0 | 3.0 | 3.0 | 2.7 | 2.7 | 3.0 | 3.0 | 3.0 | 3.0 | 3.0 | 3.0 | 3.0 | 3.0 |

TABLE 3

|  |  | (% by weight) Comparative Example | | | | | |
|---|---|---|---|---|---|---|---|
|  |  | 1 | 2 | 3 | 4 | 5 | 6 |
| Water phase | Common salt | 0.3 | 0.3 | 0.3 | 3.0 | 1.2 | 1.8 |
|  | Sucrose | 1.0 | 1.0 | 1.0 | 1.0 | 6.0 | 1.5 |
|  | Condiment | 0.4 | 0.4 | 0.4 | 0.5 | — | 0.5 |
|  | Mustard powder | 0.2 | 0.2 | 0.2 | 0.3 | 0.2 | 0.3 |
|  | Thickener *1 | 0.2 | 0.2 | 0.2 | 0.6 | — | 0.6 |
|  | Thickener *2 | — | — | — | — | — | — |
|  | Thickener *3 | — | — | — | — | 1.5 | 2.0 |
|  | Soybean protein | — | — | — | 1.5 | — | — |
|  | Enzyme-treated yolk 1 | 20.0 | 20.0 | 20.0 | — | — | — |
|  | Enzyme-treated yolk 2 | — | — | — | — | 7.0 | — |
|  | Enzyme-treated yolk 3 | — | — | — | — | — | 20.0 |
|  | Enzyme-treated yolk powder | — | — | — | — | — | — |
|  | Yolk | — | — | — | — | — | — |
|  | 10% Brewed vinegar | 6.0 | 6.0 | 6.0 | 9.0 | 9.5 | 9.0 |
|  | Water | 1.9 | 1.9 | 1.9 | 29.1 | 30.6 | 34.3 |
| Oil phase | Oil Composition 1 | 21.0 | 35.0 | 20.8 | 16.5 | 13.2 | 9.0 |
|  | Oil Composition 2 | 49.0 | 35.0 | 48.8 | 38.5 | 30.8 | 21.0 |
|  | Polyglycerol fatty acid ester *4 | — | — | 0.4 | — | — | — |
|  | Sorbitan fatty acid ester *5 | — | — | — | — | — | — |
|  | Sucrose fatty acid ester *6 | — | — | — | — | — | — |
| Lyso proportion (%) |  | 45 | 50 | 50 | — | 55 | 50 |
| Evaluation 5° C. | Appearance | 3.0 | 3.0 | 3.0 | 3.0 | 3.0 | 3.0 |
|  | Physical property | 3.0 | 3.0 | 3.0 | 3.0 | 3.0 | 3.0 |
| 0° C. | Appearance | 3.0 | 2.0 | 3.0 | 3.0 | 3.0 | 3.0 |
|  | Physical property | 2.5 | 1.5 | 3.0 | 3.0 | 3.0 | 3.0 |
| −5° C. | Appearance | 1.0 | 1.0 | 1.0 | 2.0 | 2.5 | 2.7 |
|  | Physical property | 1.0 | 1.0 | 1.0 | 2.0 | 2.5 | 2.7 |
| Cycle test | Appearance | 3.0 | 3.0 | 3.0 | 3.0 | 3.0 | 3.0 |
|  | Physical property | 3.0 | 3.0 | 3.0 | 3.0 | 3.0 | 3.0 |

*1 Xanthan gum (product of DAINIPPON PHARMACEUTICAL CO., LTD).
*2 Tamarind gum (product of DAINIPPON PHARMACEUTICAL CO., LTD).
*3 INSTANT PURE-FLO (product of National Starch and Chemical Company).
*4 Average polymerization degree: 10; degree of esterification: at least 80%; fatty acid composition: C18 and C22: 1; HLB: 2.0.
*5 Fatty acid composition: C18; HLB: 2.1.
*6 Fatty acid composition: C18 and C2; degree of esterification of C18: at least 60%; acetylation rate: at least 35%; HLB: 0.

Comparative Examples 1 and 2 relate to mayonnaise devoid of crystallization inhibitors, and both mayonnaise samples underwent demulsification (oil-off) after storage for 1 month at −5° C. and 0° C. and caused separation, surface roughness and water separation. Comparative Example 3 relates to mayonnaise in which excessive amount of polyglycerol fatty acid ester (0.4% by weight) was used in the oil phase. Sufficient emulsion stability was unable to be achieved in this mayonnaise On the other hand, when a proper amount of polyglycerol fatty acid ester (Examples 1 to 3 and 6 to 8), sorbitan fatty acid ester (Example 4) or sucrose fatty acid ester (Example 5) was used as crystallization inhibitor, no demulsification was observed even after storage for 1 month at −5° C. to 5° C., and both appearance and physical property were good.

Emulsion stability tends to be improved when the ratio of oil phase is lowered, but sufficient improvement cannot be obtained in the absence of crystallization inhibitor. When used in a proper amount, the crystallization inhibitor was able to bring sufficient improvement in the emulsion stability (Examples 11 to 13 and Comparative Examples 4 to 6).

Furthermore, the polyglycerol fatty acid ester (Examples 1 to 3 and 6 to 8) was confirmed to be the best use as a crystallization inhibitor agent both in appearance and physical property, from results of the tests under programmed temperature.

Examples 14 to 16

French dressing (Example 14), Thousand Island dressing (Example 15) and sesame dressing (Example 16) were produced with their corresponding compositions shown in Table 4. More specifically, raw materials for an oil phase were added dropwise to a water phase under stirring to conduct preliminary emulsification. This emulsion was homogenized by a homomixer to obtain the respective dressing samples having an average emulsified droplet diameter of 4 to 12 μm. With respect to the respective dressing samples, the same evaluation as in Example 1 was conducted by 6 panelists. As a result, all the dressing samples were good in both appearance and physical property even after storage for 1 month at −5° C. to 5° C. as shown in Table 4.

TABLE 4

|  |  | (% by weight) Example | | |
|---|---|---|---|---|
|  |  | 14 | 15 | 16 |
| Water phase | Common salt | 3.0 | 2.0 | 2.5 |
|  | Sucrose | 5.0 | 5.0 | 11.0 |
|  | Condiment | 0.5 | 0.5 | 1.0 |
|  | Lemmon juice | 2.0 | 2.0 | — |
|  | Thickener *1 | 0.6 | 0.4 | 0.01 |
|  | Enzyme-treated yolk 1 | 2.0 | 4.0 | — |
|  | Yolk | — | — | 1.5 |
|  | Tomato ketchup | — | 5.0 | — |
|  | Pickles | — | 4.0 | — |
|  | Tomato paste | — | 1.0 | — |

TABLE 4-continued

|  |  | (% by weight) Example | | |
|---|---|---|---|---|
|  |  | 14 | 15 | 16 |
|  | Miso | — | — | 4.0 |
|  | Pounded sesame | — | — | 7.0 |
|  | Soy | — | — | 3.0 |
|  | 5% Brewed vinegar | 14.0 | 14.0 | 14.0 |
|  | Water | 32.9 | 27.1 | 25.99 |
| Oil phase | Oil Composition 1 | 19.5 | 17.0 | 14.5 |
|  | Oil Composition 2 | 19.5 | 17.0 | 14.5 |
|  | Polyglycerol fatty acid ester *2 | 1.0 | 1.00 | 1.0 |
| Lyso proportion (%) |  | 40 | 40 | — |
| Evaluation 5° C. | Appearance | 3.0 | 3.0 | 3.0 |
|  | Physical property | 3.0 | 3.0 | 3.0 |
| 0° C. | Appearance | 3.0 | 3.0 | 3.0 |
|  | Physical property | 3.0 | 3.0 | 3.0 |
| −5° C. | Appearance | 3.0 | 3.0 | 3.0 |
|  | Physical property | 3.0 | 3.0 | 3.0 |

*1 Xanthan gum (product of DAINIPPON PHARMACEUTICAL CO., LTD).
*2 Average polymerization degree: 10; degree of esterification: at least 80%; fatty acid composition: C18: 1 and C16.

Industrial Applicability

As described above, the acidic oil-in-water type emulsion compositions according to the present invention are so excellent in shelf stability at low temperatures that they do not crack during storage at a low temperature in a refrigerator though they contain DAG at a high concentration, also good in appearance and flavor and useful as diets or lipid metabolism-improving foods.

What is claimed is:

1. An acidic oil-in-water type emulsion composition comprising an oil phase containing at least 20% by weight of diacylglycerol and 0.5 to 5.0% by weight of crystallization inhibitor.

2. The acidic oil-in-water type emulsion composition according to claim 1, wherein the crystallization inhibitor is selected from polyglycerol fatty acid esters, sucrose fatty acid esters and sorbitan fatty acid esters.

3. The acidic oil-in-water type emulsion composition according to claim 2, wherein the polyglycerol fatty acid esters are such that the average polymerization degree of glycerol is 2 to 12, the number of carbon atoms in the fatty acid moiety is 12 to 22, and the degree of esterification is at least 70%.

4. The acidic oil-in-water type emulsion composition according to claim 2, wherein the sucrose fatty acid esters are such that the degree of esterification with a fatty acid having 12 to 22 carbon atoms is at least 50%, and the remaining hydroxyl groups (not esterified with above-mentioned fatty acids) are acetylated.

5. The acidic oil-in-water type emulsion composition according to claim 2, wherein the sorbitan fatty acid esters are those in which the number of carbon atoms in the fatty acid composition is 12 to 22, and the HLB is lower than 3.

6. The acidic oil-in-water type emulsion composition according to any one of claims 1 to 5, which further comprises egg yolk.

* * * * *